United States Patent [19]

Oppenlaender et al.

[11] Patent Number: 5,147,644

[45] Date of Patent: Sep. 15, 1992

[54] USE OF MIXTURES OF POLYGLYCEROL FATTY ESTERS AS EMULSIFIERS IN COSMETIC AND PHARMACEUTICAL FORMULATIONS

[75] Inventors: Knut Oppenlaender, Ludwigshafen; Brigette Wegner, Speyer; Karl Stork, Carlsberg; Franz Frosch, Duerkheim; Hans-Ulrich Wekel, Ellerstadt, all of Fed. Rep. of Germany

[73] Assignee: BASF Aktiengesellschaft, Ludwigshafen, Fed. Rep. of Germany

[21] Appl. No.: 659,254

[22] Filed: Feb. 22, 1991

[30] Foreign Application Priority Data

Feb. 23, 1990 [DE] Fed. Rep. of Germany ....... 4005819
Jul. 25, 1990 [DE] Fed. Rep. of Germany ....... 4023593

[51] Int. Cl.$^5$ ............................................... A61K 7/48
[52] U.S. Cl. .............................. 424/401; 424/DIG. 5; 514/785; 514/786; 514/937; 514/938; 514/939
[58] Field of Search .................. 424/401, DIG. 5; 514/785, 786, 937, 938, 939

[56] References Cited

U.S. PATENT DOCUMENTS

| | | |
|---|---|---|
| 3,890,358 | 6/1975 | Hutchison et al. ............... 424/64 X |
| 4,216,201 | 8/1980 | Calvo ................................. 424/63 |
| 4,454,113 | 6/1984 | Hemker ............................. 424/63 |
| 4,680,184 | 7/1987 | Selden et al. ..................... 426/654 |
| 4,690,774 | 9/1987 | Vishnupad et al. ............... 252/309 |
| 4,704,271 | 11/1987 | Hourihan et al. ................ 424/66 |

FOREIGN PATENT DOCUMENTS

0069412 1/1983 European Pat. Off. .
0070080 1/1983 European Pat. Off. .
0203831 12/1986 European Pat. Off. .

OTHER PUBLICATIONS

J. Soc. Cosmet, Chem., 28, pp. 733-740, Dec. 1977, J. P. McCarthy, et al., "Development of Water-in-Oil Emulsifiers and Their Application to Cosmetic Emulsions".

62-Essential Oils, Chem. Abst., 93:53797s, 1980, & JP-A-80/31,038, Mar. 5, 1980.

Emulgatoren fur Lebensmittel, 1985, pp. 154-161, G. Schuster.

Primary Examiner—Thurman K. Page
Assistant Examiner—R. Harrison
Attorney, Agent, or Firm—Oblon, Spivak, McClelland, Maier & Neustadt

[57] ABSTRACT

Mixtures of polyglycerol fatty esters obtainable by partial esterification of a polyglycerol mixture consisting of
from 0 to 5% by weight of monoglycerol,
from 15 to 40% by weight of diglycerol,
from 30 to 55% by weight of triglycerol,
from 10 to 25% by weight of tetraglycerol,
from 0 to 15% by weight of pentaglycerol,
from 0 to 10% by weight of hexaglycerol and
from 0 to 5% by weight of higher polyglycerols
with one or more saturated fatty acids of 12 to 22 carbon atoms or one or more unsaturated fatty acids of 16 to 22 carbon atoms, where the unsaturated fatty acid or fatty acid mixture used may furthermore contain up to 10% by weight of saturated fatty acids of 16 to 22 carbon atoms and the degree of esterification of the saturated or unsaturated fatty acids in the mixture is from 20 to 70%, are used as emulsifiers in cosmetic and pharmaceutical formulations.

8 Claims, No Drawings

USE OF MIXTURES OF POLYGLYCEROL FATTY ESTERS AS EMULSIFIERS IN COSMETIC AND PHARMACEUTICAL FORMULATIONS

The present invention relates to the use of mixtures of polyglycerol fatty esters which are obtainable by partial esterification of a polyglycerol mixture consisting of
from 0 to 5% by weight of monoglycerol,
from 15 to 40% by weight of diglycerol,
from 30 to 55% by weight of triglycerol,
from 10 to 25% by weight of tetraglycerol,
from 0 to 15% by weight of pentaglycerol,
from 0 to 10% by weight of hexaglycerol and
from 0 to 5% by weight of higher polyglycerols
with one or more saturated fatty acids of 12 to 22 carbon atoms or one or more unsaturated fatty acids of 16 to 22 carbon atoms, where the unsaturated fatty acid or fatty acid mixture used may furthermore contain up to 10% by weight of saturated fatty acids of 16 to 22 carbon atoms and the degree of esterification of the saturated or unsaturated fatty acids in the mixture is from 20 to 70%, as emulsifiers in cosmetic and pharmaceutical formulations.

The present invention furthermore relates to cosmetic and pharmaceutical formulations which contain these mixtures as emulsifiers.

EP-B 069 412 (1) relates to a dietary beverage concentrate which, in addition to other constituents, contains a polyglycerol fatty ester emulsifier having on average from 2 to 10 glycerol units and from 1 to 3 fatty acid groups of 14 to 18 carbon atoms per glycerol unit. Fatty acids mentioned are saturated fatty acids, and stearic acid is not mentioned explicitly.

U.S. Pat. No. 4 680 184 (2) describes emulsifier compositions for bakery products, which compositions contain, inter alia, fatty esters of polyols, such as polyglycerol having from 4 to 14 hydroxyl groups, from 10 to 66% of the hydroxyl groups having been esterified with saturated $C_{14}$–$C_{20}$-fatty acids, such as palmitic or stearic acid, or trans-unsaturated $C_{16}$–$C_{20}$-fatty acids.

EP-A 203 831 (3) relates to polyglycerol fatty ester emulsifiers which predominantly consist of mono- and diesters of saturated fatty acids having on average from 13 to 16.5 carbon atoms. These emulsifiers are recommended for the food sector.

J. Soc. Cosmet Chem. 28 (December 1977), 733–740 (4) describes polyglycerol esters as water-in-oil emulsifiers for cosmetic formulations. Octaglyceryl pentaoleate and glyceryl trioleate are mentioned as oleic esters.

In Fette, Seifen, Anstrichmittel, 88th year, No. 3 (1986), 101–106 (5), monoesters to tetraesters of fatty acids with diglycerol are recommended as emulsifiers for the food industry and cosmetics.

JP-A 80/031 038 (6), cited in Chem. Abstr. 93 (1980), 53797s, describes creams and lotions of the water-in-oil type which contain dextrin, diglyceryl monooleate and diglyceryl dioleate.

In addition to the diglycerol fatty esters, triglycerol fatty esters and triglyceryl oleates are also widely used in the area of cosmetics.

EP-B 070 080 (7) relates to a process for the preparation of a fat, in particular a margarine fat material, using a polyglycerol fatty ester, wherein (i) the polyglycerol content consists of from 50 to 100% of di-, tri- or tetraglycerol, from 0 to 40% of penta- or hexaglycerol and from 0 to 10% of heptaglycerol or higher polymers, (ii) the fatty acid radicals, which are preferably saturated, are selected from those of 16 to 18 carbon atoms and mixtures thereof and have an iodine number which does not exceed 10, and (iii) the degree of esterification is from 80 to 100%.

The monograph Emulgatoren für Lebensmittel, edited by G. Schuster, Springer-Verlag Berlin, Heidelberg, New York, Tokyo, 1985 (8), states on pages 160/161, in connection with surfactant properties of polyglycerol esters, that the substances act as water-in-oil emulsifiers when all or the predominant number of the hydroxyl groups are esterified but as oil-in-water emulsifiers when they are present as mono- or diesters, i.e. when the degree of esterification is low.

The emulsifiers usually used for cosmetic and pharmaceutical formulations are frequently the cause of an insufficient shelf life of the formulations. Thus, precipitates or more or less complete phase separations often occur in the prepared creams. Furthermore, it is desirable to reduce the amount of emulsifiers used while maintaining constant activity.

It is an object of the present invention to provide emulsifiers for cosmetic and pharmaceutical formulations, which emulsifiers act mainly as water-in-oil emulsifiers and do not have the deficiencies described.

We have found that this object is achieved by the use, defined at the outset, of mixtures of polyglycerol fatty esters as emulsifiers in cosmetic and pharmaceutical formulations.

In a preferred embodiment, a mixture of polyglycerol fatty esters which is obtainable by partial esterification of a polyglycerol mixture consisting of
from 0 to 5% by weight of monoglycerol,
from 20 to 40% by weight of diglycerol,
from 35 to 55% by weight of triglycerol,
from 10 to 20% by weight of tetraglycerol,
from 5 to 10% by weight of pentaglycerol,
from 1 to 5% by weight of hexaglycerol and
from 0 to 5% by weight of higher polyglycerols
is used.

Particularly suitable saturated fatty acid components are lauric acid, tridecanoic acid, myristic acid, palmitic acid, margarinic acid, stearic acid, arachic acid and behenic acid and mixtures thereof. Naturally occurring mixtures are, for example, the coconut fatty acids, which contain lauric acid as the main constituent and also saturated $C_{14}$–$C_{18}$-fatty acids and may contain small amounts of saturated $C_8$–$C_{10}$-fatty acids and unsaturated fatty acids, and tallow fatty acids which are essentially a mixture of palmitic acid and stearic acid. A mixture which consists of not less than 40, preferably 60 to 99, % by weight of stearic acid is particularly preferred.

Suitable unsaturated fatty acid components are monoolefinically unsaturated acids, for example hexadecenoic acids, octadecenoic acids, such as oleic acid (cis-9-octadecenoic acid) or elaidic acid (trans-9-octadecenoic acid), eicosenoic acids and docosenoic acids, such as erucic acid (cis-13-docosenoic acid) or brassidic acid (trans-13-docosenoic acid), polyunsaturated fatty acids, for example octadecadienoic acids and octadecatrienoic acids, such as linoleic acid and linolenic acid, and mixtures thereof. The best results are obtained with a fatty acid or fatty acid mixture which consists of not less than 60, preferably from 65 to 99, % by weight of oleic acid or erucic acid.

As a result of their preparation or isolation from naturally occurring fatty acid mixtures, the unsaturated fatty acid or fatty acid mixture used may also contain up to 10, preferably up to 5, % by weight of saturated fatty acids of 16 to 22 carbon atoms, for example palmitic acid or stearic acid.

The polyglycerols are only partially esterified, the degree of esterification of the mixture being from 20 to 70%. Particularly good results are obtained with a degree of esterification of from 25 to 50%, in particular from 30 to 40%.

The mixtures of polyglycerol fatty esters of saturated fatty acids may also contain up to 10% by weight, based on the amount of fatty acids used, of free fatty acids or their salts.

The mixtures of polyglycerol fatty esters of saturated fatty acids are particularly suitable as oil-in-water emulsifiers in cosmetic and pharmaceutical formulations.

The novel emulsifiers based on saturated fatty acids give particularly good results when they are used together with up to 100, preferably up to 60, % by weight, based on the amount of emulsifier, of a monoglycerol fatty monoester, for example glyceryl monostearate.

The mixtures of the polyglycerol fatty esters of unsaturated fatty acids are particularly suitable as water-in-oil emulsifiers in cosmetic and pharmaceutical formulations.

The polyglycerol fatty ester mixtures are advantageously prepared by subjecting the corresponding polyglycerol mixture to an esterification reaction with the desired fatty acid or fatty acid mixture by a conventional method. The reaction is carried out as a rule in the presence of an acidic or basic esterification catalyst, such as hypophosphorous acid, phosphorous acid, sulfuric acid, p-toluenesulfonic acid, citric acid, sodium methylate or a soap.

The polyglycerol mixtures are usually obtainable according to literature reference (5), by alkali-catalyzed condensation of glycerol at elevated temperatures or according to DE-A-3,842,692 (9), by reacting glycerol with epichlorohydrin in the presence of an acidic catalyst at elevated temperatures. However, corresponding pure polyglycerol components may also be mixed with one another.

The present invention furthermore relates to cosmetic and pharmaceutical formulations which contain, as an emulsifier, a mixture of this type consisting of polyglycerol fatty esters in an amount of from 0.1 to 20, preferably from 0.5 to 10, in particular from 1 to 5, % by weight, based on the total amount of the formulation. In particular, cosmetic formulations which contain these emulsifiers have substantially improved properties.

Suitable cosmetic formulations to which a readily spreadable consistency is imparted by the use of oil-in-water or water-in-oil emulsifiers, because these emulsifier systems enable an oil or a fat to be easily incorporated in an aqueous phase or an aqueous phase to be easily incorporated in an oil or a fat, are, for example, creams such as care creams, baby creams or sunscreen creams, ointments, lotions or make-up. In pharmaceutical formulations, such as ointments or creams, oil-in-water or water-in-oil emulsifiers are required for application of active compounds.

The conventional formulations and components as well as the usual assistants and additives, such as stabilizers or preservatives for such cosmetic and pharmaceutical formulations, are known to the skilled worker and therefore need not be described in detail here.

Compared with the prior art, the polyglycerol fatty ester mixtures used according to the invention ensure a substantially longer shelf life of the cosmetic and pharmaceutical formulations emulsified using the said mixtures, which is particularly important in the case of water-in-oil emulsions, which are more difficult to stabilize than oil-in-water emulsions. Furthermore, lower concentrations of the polyglycerol fatty ester mixtures are generally required in the formulations in order to obtain the same effect as that obtained with prior art agents.

In most cases, the polyglycerol fatty ester mixtures need not be subsequently bleached after their preparation since they are generally obtained in sufficiently pure form in their preparation. Dispensing with bleaches is of great importance in cosmetic and pharmaceutical formulations, for example because of the better toleration of such formulations on the skin or in the body.

EXAMPLE 1

Preparation of a polyglyceryl stearate mixture 1417.5 g of (corresponding to 7.0 mol, based on a cryoscopically determined mean molecular weight) of a polyglycerol mixture which was obtained by alkali metal hydroxide-catalyzed condensation of glycerol and, according to gas chromatographic analysis, consisted of 35% by weight of diglycerol,
39% by weight of triglycerol,
18% by weight of tetraglycerol,
5% by weight of pentaglycerol,
2% by weight of hexaglycerol,
0.6% by weight of heptaglycerol,
0.3% by weight of octaglycerol and
0.1% by weight of nonaglycerol, together with 3335.5 g of technical-grade stearic acid composed of 63% by weight of stearic acid, 28% by weight of palmitic acid, 3% by weight of margarinic acid, 5% by weight of saturated fatty acids of less than 16 carbon atoms and 1% by weight of saturated fatty acids of more than 18 carbon atoms (corresponding to 12.0 mol, based on the measured acid number of 202 mg KOH/g) and 46 g of 50% strength by weight hypophosphorous acid, were heated to 180° C. under nitrogen as a protective gas and stirred at this temperature for 22 hours. During this time, about 210 g of the water of reaction formed were distilled off. Thereafter, the mixture had an acid number of less than 10.

After cooling to 90°–95° C. the reaction mixture was neutralized with 51 g of 50% strength by weight sodium hydroxide solution. After stirring for 1 hour at the stated temperature and subsequent hot filtration, 4360 g of a polyglyceryl stearate mixture were obtained as a colorless, waxy product having a degree of hydrolysis of 143, corresponding to a degree of esterification of from 35 to 45%.

EXAMPLE 2

Preparation of a polyglyceryl tallow fatty ester mixture

A mixture of 161.2 g (corresponding to 0.8 mol, based a cryoscopically determined mean molecular weight) of the polyglycerol mixture characterized in Example 1, 376.7 g of a hardened tallow fatty acid composed of 64% by weight of stearic acid, 27% by weight of palmitic acid, 2% by weight of margarinic acid, 4% by weight of saturated fatty acids of less than 16 carbon atoms, 2% by weight of saturated fatty acids of more than 18 carbon atoms, and 1% by weight of unsaturated fatty acids (corresponding to 1.4 mol, based on the measured acid number of 208 mg KOH/g) and 2.7 g of 50% strength by weight hypophosphorous acid were heated to 180° C. under nitrogen. At this temperature, the water of reaction formed was distilled off in the course of 17 hours. Thereafter, the mixture had an acid number of less than 5.

After cooling to about 90° C., the reaction mixture was neutralized with 50% strength by weight sodium hydroxide solution. Hot filtration gave 515 g of polyglycerol tallow fatty ester mixture as a pale yellow waxy product having an iodine color number of from 1 to 3 and a degree of esterification of from 35 to 40%.

EXAMPLE 3

Preparation of a polyglyceryl oleate mixture 292 g (corresponding to 1.45 mol, based on a cryoscopically determined mean molecular weight) of a polyglycerol mixture which was obtained by alkali metal hydroxide-catalyzed condensation of glycerol and, according to gas chromatographic analysis, consisted of
35% by weight of diglycerol,
39% by weight of triglycerol,
18% by weight of tetraglycerol,
5% by weight of pentaglycerol,
2% by weight of hexaglycerol,
0.6% by weight of heptaglycerol,
0.3% by weight of octaglycerol and
0.1% by weight of nonaglycerol,
together with 696 g of technical-grade oleic acid (67% by weight of oleic acid, 12% by weight of linoleic acid, 5% by weight of hexadecenoic acid, 2% by weight of stearic acid, 1% by weight of linolenic acid and 1% by weight of palmitic acid) and 10 g of hypophosphorous acid, were heated to 180° C. under nitrogen as a protective gas. At this temperature, the resulting water of reaction was distilled off in the course of 12 hours. After cooling to 80°-90° C., the reaction mixture was neutralized with 50% strength by weight sodium hydroxide solution. Filtration gave 780 g of a polyglyceryl oleate mixture as a pale yellow, viscous liquid having an iodine color number of from 3 to 5 and a hydrolysis number of 145, corresponding to a degree of esterification of from 35 to 40%.

EXAMPLE 4

Preparation of a polyglyceryl erucate mixture

A mixture of 141 g (corresponding to 0.7 mol) of the polyglycerol mixture characterized in Example 1, 403 g of technical-grade erucic acid (92% by weight of erucic acid, 5% by weight of eicosenoic acid and 2% by weight of octadecenoic acid) and 2.7 g of hypophosphorous acid was heated to 180° C. under nitrogen. At this temperature, the resulting water of reaction was distilled off in the course of 21 hours. After cooling to 80°-90° C., the reaction mixture was neutralized with 50% strength by weight sodium hydroxide solution. Filtration at 80°-90° C. gave 510 g of a polyglyceryl erucate mixture as a pale yellow, waxy solid having an iodine color number of from 4 to 6 and a degree of esterification of from 35 to 40%.

COMPARATIVE EXAMPLE A

Preparation of a polyglycerol fatty ester mixture

A mixture of 194 g (corresponding to 1.0 mol, based on a cryoscopically determined mean molecular weight) of a polyglycerol mixture which was obtained by alkali metal hydroxide-catalyzed condensation of glycerol and, according to gas chromatographic analysis, consisted of
47% by weight of diglycerol,
25% by weight of triglycerol,
14% by weight of tetraglycerol,
8% by weight of pentaglycerol,
4% by weight of hexaglycerol,
1.3% by weight of heptaglycerol,
0.5% by weight of octaglycerol and
0.2% by weight of nonaglycerol,
364 g of palm kernel oil fatty acid and 2.8 g of p-toluenesulfonic acid monohydrate was heated at 230° C. for 3 hours as described in Example 1 of (4), the resulting water of reaction being distilled off. Thereafter, further esterification was carried out at 100° C. with 238 g of a 50% strength by weight aqueous citric acid solution in the course of 2 hours, the citric acid was separated off and the crude product was bleached with 20 g of a 30% strength by weight aqueous hydrogen peroxide solution. 450 g of a polyglycerol fatty ester mixture were obtained as a dark, viscous liquid having an iodine color number of >150 and an acid number of 3.3, a hydrolysis number of 200 and a degree of esterification of from 45 to 50%.

Testing of performance characteristics of polyglycerol fatty ester mixtures based on saturated fatty acids.

Cosmetic formulations in cream form having the following compositions were investigated with regard to their shelf life. The emulsifiers used in each case were the substances stated in Table 1.

| Composition 1 (oil-in-water emulsion) | | |
|---|---|---|
| Fat phase | | |
| (31% by weight): | 5.0% | by weight of emulsifier |
| | 3.0% | by weight of glyceryl monostearate |
| | 3.0% | by weight of cetyl alcohol |
| | 10.0% | by weight of cetostearyl 2-ethylhexanoate |
| | 10.0% | by weight of liquid paraffin |
| Assistants | | |
| (3.5% by weight): | 3.0% | by weight of propylene glycol |
| | 0.2% | by weight of methyl- and propylparaben |
| | 0.3% | by weight of imidazolidinylurea |
| Water: | 65.5% | by weight |

Composition 2 (oil-in-water emulsion)

As for Composition 1, but with 20.0% by weight of peanut oil instead of 10.0% by weight of cetostearyl 2-ethylhexanoate and 10% by weight of liquid paraffin.

Composition 3 (oil-in-water emulsion)

As for Composition 1, but with 20.0% by weight of jojoba oil instead of 10.0% by weight of cetostearyl 2-ethylhexanoate and 10% by weight of liquid paraffin The results of the stability investigations are shown in Table 1. The rating scheme shows that the formulations containing the novel emulsifiers give excellent results on storage, with regard to phase stability and the occurrence of secondary odor.

TABLE 1

Stability of cosmetic formulations in cream form

| Emulsifier | Stability after 6 weeks at 20° C. | after 6 weeks at 45° C. | after 12 weeks at 20° C. | after 12 weeks at 45° C. |
|---|---|---|---|---|
| Composition 1: | | | | |
| Polyglyceryl stearate mixture from Example 1 | 1 | 1–2 | 2 | 1–2 |
| Composition 2: | | | | |
| Polyglyceryl stearate mixture from Example 1 | 1 | 1 | 1 | 4 |
| Composition 3: | | | | |
| Polyglyceryl stearate mixture from Example 1 | 1 | 1 | 1 | 3–4 |

Rating scheme:
1 = stable emulsion without secondary odor
2 = slightly inhomogenous emulsion, very slight secondary odor
3 = incipient precipitation, slight secondary odor
4 = substantial precipitation, strong secondary odor
5 = phase separation Testing of performance characteristics of polyglycerol fatty ester mixtures based on unsaturated fatty acids.

Cosmetic formulations in cream form having the following compositions were investigated with regard to their shelf life in comparison with formulations emulsified using a prior art agent. The emulsifiers used in each case were the substances stated in Table 2.

| Composition 4 Fat phase | | |
|---|---|---|
| (28% by weight): | 1.0% | by weight of emulsifier |
| | 10.0% | by weight of liquid paraffin |
| | 10.0% | by weight of cetostearyl 2-ethyl-hexanoate |
| | 3.0% | by weight of microcrystalline wax |
| | 3.0% | by weight of beeswax |
| | 0.5% | by weight of aluminum stearate |
| | 0.5% | by weight of magnesium stearate |
| Assistants | | |
| (4% by weight): | 0.5% | by weight of magnesium sulfate |
| | 3.0% | by weight of propylene glycol |
| | 0.3% | by weight of imidazolidinylurea |
| | 0.2% | by weight of methyl- and propyl-paraben |
| Water: | 68.0% | by weight |
| Composition 5 Fat phase | | |
| (52% by weight): | 5.0% | by weight of emulsifier |
| | 10.0% | by weight of liquid paraffin |
| | 20.0% | by weight of cetostearyl 2-ethyl-hexanoate |
| | 10.0% | by weight of hydrogenated polyisobutene |
| | 3.0% | by weight of microcrystalline wax |
| | 3.0% | by weight of beeswax |
| | 0.5% | by weight of aluminum stearate |
| | 0.5% | by weight of magnesium stearate |
| Assistants | | |
| (4% by weight): | 0.5% | by weight of magnesium sulfate |
| | 3.0% | by weight of propylene glycol |
| | 0.3% | by weight of imidazolidinylurea |
| | 0.2% | by weight of methyl- and propyl-paraben |
| Water: | 44.0% | by weight |

Composition 6

As for Composition 1 but with 3.0% by weight of emulsifier (fat phase: 30% by weight) and 66.0% by weight of water.

The results of the stability tests are shown in Table 2. From the rating scheme, it is evident that, on storage, the formulations containing the emulsifiers used according to the invention give substantially better results with regard to phase stability and occurrence of secondary odor compared with the formulations which contain a prior art agent as an emulsifier.

The attempt to use a polyglycerol fatty ester mixture according to Comparative Example A as an emulsifier was unsuccessful because both water-in-liquid paraffin or water-in-peanut oil emulsions treated with said mixture and cream formulations of Composition 1 or 2 in which this polyglycerol fatty ester mixture had been incorporated separated into the individual phases again within 24 hours.

TABLE 2

Stability of cosmetic formulations in cream form

| Emulsifier | Stability after 6 weeks at 20° C. | after 6 weeks at 45° C. | after 12 weeks at 20° C. | after 12 weeks at 45° C. |
|---|---|---|---|---|
| Composition 4: | | | | |
| Polyglyceryl oleate mixture from Example 3 | 1 | 1 | 1–2 | 3 |
| Mixture of triglyceryl mono- and dioleate* for comparison | 2 | 3–4 | 3 | 3–4 |
| Composition 5: | | | | |
| Polyglyceryl oleate mixture from Example 3 | 1 | 1–2 | 1 | 2 |
| Mixture of triglyceryl mono- and dioleate* for comparison | 1 | 3 | 1–2 | 4 |
| Composition 6: | | | | |
| Polyglyceryl oleate mixture from Example 3 | 1–2 | 1–2 | | |
| Polyglyceryl erucate mixture form Example 4 | 1–2 | 1–2 | | |

*Commercial product Caprol 3 GO from Capitol City Products Comp., US
Rating scheme:
1 = Stable emulsion without secondary odor
2 = Slightly inhomogenous emulsion, very slight secondary odor
3 = Incipient precipitation, slight secondary odor
4 = Substantial precipitation, strong secondary odor
5 = Phase separation

We claim:

1. A process for emulsifying immiscible phases in cosmetic and pharmaceutical formulations, wherein a mixture of polyglycerol fatty esters is used for this purpose, said mixture being obtainable by partial esterification of a polyglycerol mixture consisting of
from 0 to 5% by weight of monoglycerol,
from 15 to 40% by weight of diglycerol,
from 30 to 55% by weight of triglycerol,
from 10 to 25% by weight of tetraglycerol,
from 0 to 15% by weight of pentaglycerol,
from 0 to 10% by weight of hexaglycerol and
from 0 to 5% by weight of higher polyglycerols
with one or more saturated fatty acids of 12 to 22 carbon atoms or one or more unsaturated fatty acids of 16 to 22 carbon atoms, where the unsaturated fatty acid or fatty acid mixture used may furthermore contain up to 10% by weight of saturated fatty acids of 16 to 22 carbon atoms and the degree of esterification of the saturated or unsaturated fatty acids in the mixture is from 20 to 70%, as an emulsifier in cosmetic and pharmaceutical formulations.

2. A process as claimed in claim 1, wherein a polyglycerol mixture consisting of from 0 to 5% by weight of monoglycerol,
from 20 to 40% by weight of diglycerol,
from 35 to 55% by weight of triglycerol,
from 10 to 20% by weight of tetraglycerol,
from 5 to 10% by weight of pentaglycerol,
from 1 to 5% by weight of hexaglycerol and
from 0 to 5% by weight of higher polyglycerols,
is used as a starting material.

3. A process as claimed in claim 1, wherein the partial esterification is carried out with a saturated fatty acid or fatty acid mixture which consists of not less than 40% by weight of stearic acid.

4. A process as claimed in claim 1, wherein the partial esterification is carried out with an unsaturated fatty acid or fatty acid mixture which consists of not less than 60% by weight of oleic acid or erucic acid.

5. A process as claimed in claim 1, wherein the degree of esterification of the polyglycerol mixture is from 25 to 50%.

6. A process as claimed in claim 1, wherein a mixture of polyglycerol fatty esters of saturated fatty acids is used as an oil-in-water emulsifier in cosmetic and pharmaceutical formulations.

7. A process as claimed in claim 1, wherein a mixture of polyglycerol fatty esters of unsaturated fatty acids is used as a water-in-oil emulsifier in cosmetic and pharmaceutical formulations.

8. A cosmetic or pharmaceutical formulation containing, as an emulsifier, a mixture of polyglycerol fatty esters as claimed in claim 1 in an amount of from 0.1 to 20% by weight, based on the total amount of the formulation.

* * * * *